United States Patent [19]

Koyama et al.

[11] Patent Number: 5,702,860
[45] Date of Patent: Dec. 30, 1997

[54] METHOD FOR PRODUCING NON-SPHERICAL PARTICLE

[75] Inventors: Mikio Koyama; Kenji Hayashi; Tomoe Kikuchi, all of Hino, Japan

[73] Assignee: Konica Corporation, Japan

[21] Appl. No.: 619,143

[22] Filed: Mar. 21, 1996

Related U.S. Application Data

[63] Continuation of Ser. No. 236,468, May 2, 1994, abandoned.

[30] Foreign Application Priority Data

May 18, 1993  [JP]  Japan ................................. 5-115572

[51] Int. Cl.⁶ .................................................. G03G 9/087
[52] U.S. Cl. ............................................ 430/137; 528/497
[58] Field of Search ............................ 430/137; 528/497, 528/491

[56] References Cited

U.S. PATENT DOCUMENTS

| | | | |
|---|---|---|---|
| 4,874,841 | 10/1989 | Sugimori et al. | 528/491 |
| 4,977,241 | 12/1990 | Sugimori et al. | 528/497 |
| 4,997,911 | 3/1991 | Yasui et al. | 528/496 |
| 5,344,738 | 9/1994 | Kmiecik-Lawrynowicz | 430/137 |

*Primary Examiner*—John Goodrow
*Attorney, Agent, or Firm*—Jordan B. Bierman; Bierman, Muserlian and Lucas LLP

[57] ABSTRACT

Disclosed is a method for producing non-spherical particle consisting of a number of mutually coagulated polymer particles comprising the steps of:

adding a metal salt or an aqueous solution of said metal salt, and an organic solvent being infinitely miscible with water to a dispersion of said polymer particles, wherein the concentration of said metal salt is not less than a critical coagulation concentration of said dispersion; and heating said dispersion containing said metal salt and said organic solvent with a predetermined temperature so as to coagulate said polymer particles.

18 Claims, No Drawings

METHOD FOR PRODUCING NON-SPHERICAL PARTICLE

This application is a continuation of application Ser. No. 08/236,468, filed May 02, 1994, now abandoned.

FIELD OF THE INVENTION

The present invention of non-spherical particle for use as a toner for developing electrostatic images in electrophotography, electrostatic recording, electrostatic printing and other fields or as a carrier for immobilizing a bioactive substance, and a method of producing it.

BACKGROUND OF THE INVENTION

Traditionally, commonly used toners are produced by appropriately mixing in a dry state a polymer obtained by various methods of polymerization with a coloring agent such as carbon black, a charge control agent and/or a magnetic material, then kneading the mixture in a molten state using an extruder etc., and milling and classifying it.

Other methods have been proposed in which a toner is directly produced by suspension polymerization etc.

Also proposed are methods using particles formed by emulsification polymerization [Japanese Patent Publication Open to Public Inspection (hereinafter referred to as Japanese Patent O.P.I.) Publication Nos. 220358/1985 and 284461/1992].

The toner obtained by the above-described melting kneading milling method is subject to limitation as to toner particle size control, hampering the efficient production of a toner of small particle size. In addition, uneven dispersion tends to result in a broad charge distribution. This leads to drawbacks of low resolution and high tendency for fogging and dust flight when the toner is used as a developing agent.

The direct production method based on suspension polymerization is also faulty that particle size reduction is difficult and the particle size distribution is very broad. Also, the toner produced by polymerization is usually truly spherical. The truly spherical toner has a drawback of cleaning difficulty in the electrophotographic process.

Although the methods disclosed in Japanese Patent O.P.I. Publication Nos. 220358/1985 and 284461/1992 provide non-spherical particles, particle size and particle size distribution are difficult to control, necessitating particle classification to obtain the desired particle size and particle size distribution after completion of the reaction. As for the method disclosed in Japanese Patent O.P.I. Publication No. 284461/1992, the zeta potential of pigment and polymer particles is difficult to adjust. Other drawbacks in this method are difficult particle size control because of the absence of essentially required precise specifications for the ratio of large and small particles, and insufficient mechanical strength because of a lack of strong structure of the resulting particles.

For immobilizing a bioactive substance, spherical polymer beads are commonly used as carriers.

With respect to spherical beads as bioactive substance carriers, particle size must be reduced to obtain a high surface area, resulting in drawbacks of poor handling and a very great pressure loss upon reaction mixture passage through a reactor such as a column. Increased particle size results in a decreased surface area, posing a problem of reduction in the amount of bioactive substance carried.

SUMMARY OF THE INVENTION

It is an object of the present invention to provide a non-spherical particle suitable for use as a toner for developing electrostatic images or a carrier for immobilizing a bioactive substance, more specifically an electrophotographic toner of well-controlled particle size, narrow particle size distribution and high mechanical strength which requires no process for particle size adjustment and which offers excellent resolution without significant fogging or dust flight when used as a toner for electrostatic recording.

It is another object of the present invention to provide a bioactive substance carrier which offers a sufficient surface area, a high capacity for bioactive substance carriage without significant pressure loss upon packing when used as a carrier for immobilizing a bioactive substance.

The inventors investigated various particle-coagulation type polymer toners of narrow particle size distribution broadness and high resolution which permit particle size control over a wide range and which are free of fogging and dust flight, and found that the above-described objects of the present invention can be accomplished by subjecting a polymer particle to a given treatment.

Specifically, the inventors found that a fine particle accomplishing the above-described objects can be obtained by treating a non-spherical polymer particle consisting of a number of mutually coagulated molten polymer particles with a coagulant at a concentration exceeding the critical coagulation concentration and an infinitely water-soluble organic solvent.

The inventors also found that a fine particle accomplishing the above-described objects can be obtained by adding a coagulant to the polymer particle dispersion at a concentration exceeding the critical coagulation concentration thereof, then adding an infinitely water-soluble organic solvent, and thermally melting the mixture at a temperature exceeding the glass transition point (Tg) of the polymer particles.

The inventors made further investigations based on these findings, and developed the present invention. Accordingly, the above-described objects of the present invention are accomplished by a non-spherical particle consisting of a number of mutually coagulated polymer particles treated with a coagulant at a concentration exceeding the critical coagulation concentration of the polymer particle dispersion and an infinitely water-soluble organic solvent.

The objects of the present invention are also accomplished by a method of producing a non-spherical particle consisting of a number of mutually coagulated polymer particles comprising:

a) a process for adding a metal salt or an aqueous solution thereof to a polymer particle dispersion at a concentration exceeding the critical coagulation concentration, b) a process for adding an organic solvent being infinitely miscible with water to the polymer dispersion containing the metal salt, and c) a process for heating the above mixture at a temperature exceeding the glass transition point of the polymer particles.

DETAILED DESCRIPTION OF THE INVENTION

The present invention is hereinafter described in detail.

Coagulant

The coagulant of the present invention is preferably selected from metal salts, including salts of monovalent metals such as sodium, potassium, lithium and other alkali metal salts, salts of divalent metals such as calcium, magnesium and other alkaline earth metal salts, manganese and copper, and salts of trivalent metals such as iron and aluminum. Some examples of these metal salts are given below. Examples of monovalent metal salts include sodium chloride, potassium chloride and lithium chloride. Examples of divalent metal salts include calcium chloride, zinc chloride, copper sulfate, magnesium sulfate and manganese sulfate. Examples of trivalent metal salts include aluminum chloride and iron chloride. These may be chosen as appropriate according to the purpose of their use. Generally, divalent metal salts are lower than monovalent metal salts in critical coagulation concentration (condensation value or condensation point), and trivalent metal salts have still lower critical coagulation concentrations.

In the present invention, the critical coagulation concentration is an index of dispersed particle stability in aqueous dispersion, representing the concentration at which coagulation occurs in the presence of a coagulant. The critical coagulation concentration varies widely depending on factors related to latex itself and dispersing agent. The critical coagulation concentration of a dispersion can be determined as directed by Seizo Okamura et al. in "Kobunshi Kagaku" 17, 601 (1960) and other publications. Alternatively, the critical coagulation concentration can be obtained as the salt concentration at which the zeta potential of a particle dispersion of the desired salt begins to change by adding the salt at various concentrations.

Using the metal salt of the present invention, the polymer particle dispersion is treated to have a concentration exceeding the critical coagulation concentration. For this treatment, the metal salt may be added as such or in aqueous solution, depending on the purpose of the addition. When the metal salt is added in aqueous solution, the concentration of the metal salt added per the total volume of the polymer particle dispersion and aqueous metal salt solution must exceed the critical coagulation concentration of the polymer particle dispersion.

Although the concentration of the coagulant metal salt of the present invention may be set at any level exceeding the critical coagulation concentration, it is preferable to add the metal salt at a concentration at least 1.2 times, more preferably at least 1.5 times the critical coagulation concentration.

Infinitely water-soluble organic solvent

It is preferable that the infinitely water-soluble organic solvent for the present invention does not dissolve polymer particles. Such solvents include alcohols such as methanol, ethanol, propanol, isopropanol, t-butanol, methoxyethanol, ethoxyethanol and butoxyethanol, nitriles such as acetonitrile, and dioxane.

The concentration of the infinitely water-soluble organic solvent used in the present invention is chosen as appropriate over the range 1–300% per the coagulant-containing polymer particle dispersion.

Polymer particles

Although polymer particles can usually be prepared by emulsification polymerization, suspension polymerization, dispersion polymerization, precipitation polymerization, interfacial polymerization and synthetic resin pulverization, it is preferable to prepare the polymer particles by emulsification polymerization.

A solid component relating to the present invention can easily be combined with polymer particles by, for example, suspension polymerization. Such a complex can be synthesized by dispersing a solid component relating to the present invention in the desired monomer or, if the solid component is soluble, by dissolving it in the monomer and then dispersing the solution in a dispersing agent, followed by polymerization.

As for other methods of polymerization, polymer particles combined with a solid component can be prepared by polymerizing a dispersion or solution of the solid component in a monomer, prepared by suspension polymerization as described above, by each method of polymerization.

To prepare the non-spherical particle of the present invention having a solid component combined therewith, it is preferable to use polymer particles combined with the solid component. Polymer particles combined with a solid component are obtained by dispersing a solid component relating to the present invention in the presence of a surfactant at a concentration exceeding the critical micelie concentration (CMC), diluting the resulting solid component dispersion to a surfactant concentration below the CMC, adding a radical polymerizable monomer and a radical polymerization initiator and carrying out polymerization at a given temperature.

With respect to these polymer particles, any particle size can be used, as long as it is smaller than the particle size of the desired non-spherical particle; it is preferable that the particle size of commonly used polymer particles fall within the range from about 0.01 to 10 μm.

Monomer

A hydrophobic monomer is used to obtain the polymer particle of the present invention. In addition, another monomer having an ionic dissociating group can be added as necessary. The content of the monomer having an ionic dissociating group per the total monomer content is normally about 0.1 to 30% by weight, preferably about 0.5 to 20% by weight.

The hydrophobic monomer for the present invention is exemplified by styrene and derivatives thereof such as p-methylstyrene, o-methylstyrene, p-chlorostyrene, o-chlorostyrene, p-methoxystyrene, o-methoxystyrene, p-ethoxystyrene, p-butoxystyrene, 2,4-dimethylstyrene, 2,4-dichlorostyrene, p-chloromethylstyrene, o-chloromethylstyrene, p-hydroxystyrene and p-hydroxystyrene. Also included are (meth)acrylates such as methyl (meth)acrylate, ethyl (meth)acrylate, n-butyl (meth)acrylate, 2-ethylhexyl (meth)acrylate, cyclohexyl (meth)acrylate and dodecyl (meth)acrylate. Other examples are nitrile monomers such as acrylonitrile and methacrylonitrile, vinyl ether monomers such as vinyl methyl ether and vinyl ethyl ether, vinyl ester monomers such as vinyl acetate and vinyl butyrate, olefinic monomers such as ethylene, propylene and isobutylene, and conjugated dienes such as butadiene, isoprene, chloroprene and dimethylbutadiene. These may be used single or in combination as necessary, and may be used in combination with monomers having an ionic dissociating group as described below.

The polymer particles relating to the present invention can have a polymer unit having a dissociating group.

A monomer unit having a dissociating group is defined as a monomer containing in the monomeric structure thereof a group such as a carboxyl group, a sulfonate group, a phosphonic acid group, an amino group (including primary amine, secondary amine and tertiary amine) or a quaternary ammonium salt. Specifically, monomers containing the carboxyl group include acrylic acid, methacrylic acid, maleic acid, itaconic acid, cinnamic acid, fumaric acid, maleic acid monoalkyl ester and itaconic acid monoalkyl ester. Monomers containing a sulfo group include styrenesulfonic acid, arylsulfosuccinic acid, 2-acrylamido-2-methylpropanesulfonic acid, 2-sulfoethyl methacrylate and salts thereof. Monomers containing a phosphonic acid group include acid phosphoxyethyl methacrylate, acid phosphoxypropyl methacrylate and 3-chloro-2-acid phosphoxypropyl methacrylate.

Other examples include acrylates (methacrylates) of the amino group, acrylic (methacrylic) amides, mono- or di-substitutional acrylic (methacrylic) amides substituted by an alkyl group having 1 to 18 carbon atoms on any N, vinyl compounds substituted by a heterocyclic ring having N as a member thereof, N,N-diarylalkylamines or quaternary ammonium salt thereof. Such acrylates (methacrylates) include dialkylaminoalkyl (meth)acrylates (e.g., dimethylaminoethyl acrylate, dimethylaminoethyl methacrylate, diethylaminoethyl acrylate and diethylaminoethyl methacrylate), acid salts or quaternary ammonium salts thereof, 3-dimethylaminophenyl acrylate and 2-hydroxy-3-methacryloxypropyl trimethylammonium salt.

Examples of acrylic (methacrylic) amides or mono- or di-substitutional acrylic (methacrylic) amides substituted by an alkyl group having 1 to 18 carbon atoms on any N include (meth)acrylamide, N-butyl(meth)acrylamide, N,N-diethyl (meth)acrylamide, piperazyl(meth)acrylamide and N-octadecyl(meth)acrylamide.

Examples of vinyl compounds substituted by a heterocyclic ring having N as a member thereof, N,N-diarylalkylamines or quaternary ammonium salts thereof include vinylpyridine, vinylpyrrolidone, vinylimidazole, quaternary ammonium salts thereof, N,N-diarylmethylammonium chloride and N,N-diarylethylammonium chloride.

Monomers having an active halogen, such as vinylbenzyl chloride and vinylphenetyl chloride, can also be used. For example, they may be copolymerized as such and then converted into tertiary amines or quaternary ammonium salts using appropriate amines. They may also be copolymerized as dialkylamines or quaternary ammonium salts. For example, a dialkylamine, as a monomer component, may be introduced to a vinylbenzyl chloride by an ordinary chemical reaction or polymerization reaction.

These various monomers are selected according to desired glass transition temperature, melting temperature and other factors, depending on the purpose of their use.

Radial polymerization initiator

In synthesizing the polymer particle of the present invention, a radical polymerization initiator is selected according to the method of polymerization. In the case of suspension polymerization, an oil-soluble radical polymerization initiator is used. In the case of emulsification polymerization, a water-soluble radical polymerization initiator is used. In the case of dispersion polymerization, a radical polymerization initiator is selected as appropriate according to the dispersant used, in which a water-soluble radical polymerization initiator can be used when a non-aqueous solvent or a mixed solvent of water and a water-miscible organic solvent is used.

Examples of water-soluble radical polymerization initiators include persulfates such as potassium persulfate and ammonium persulfate, water-soluble azo compounds such as azobisaminodipropane acetate, azobiscyanovaleric acid and salts thereof, and water-soluble peroxides such as hydrogen peroxide.

Examples of oil-soluble radical polymerization initiators include oil-soluble peroxides such as benzoyl peroxide and lauroyl peroxide. Oil-soluble azo series polymerization initiators include azobisisobutyronitrile and azobisvalerilonitrile. The amount of their addition can be determined according to molecular weight of the desired polymer particles and other factors. Where necessary, molecular weight regulators such as chain transfer agents, typically thiol compounds such as dodecanethiol and octylthiol are used.

With respect to the polymer particles of the present invention, Tg of the polymer particles is normally within the range from −10° C. to 120° C., preferably from 0° C. to 90° C., the softening point falling within the range 80°–220° C. The monomer composition of the polymer particles may be any one, irrespective of type and composition of other copolymerizable monomers, as long as it meets this range requirement and a polymer unit having a dissociating group is contained at about 0.1 to 20% by weight per the total polymer content.

Although the molecular weight of the polymer particles of the present invention is not subject to limitation, the weight-average molecular weight is normally 2000 to 1000000, preferably 8000 to 500000 when they are used as a toner. The molecular weight distribution is normally 1.5 to 100, preferably 1.8 to 50, as the ratio of weight-average molecular weight and number-average molecular weight (hereinafter abbreviated Mw/Mn).

Solid component

The polymer particles of the present invention can be combined with a solid component, as stated above. Various solid components can be used in this complex as necessary. Common solid components include pigments and dyes. When the polymer particles of the present invention are used as an electrophotographic toner, in particular, the above-mentioned pigments, dyes, offset prevention agent and charge control agents may be used as solid components. These may be used singly or in combination.

Pigments include inorganic pigments and organic pigments. Inorganic pigments include carbon pigments such as carbon black, graft carbon, furnace carbon and thermatomic carbon, metal oxide pigments such as magnetite, ferrite, iron oxide red, titanium oxide, zinc oxide, silica, chromium oxide, cobalt blue, ultramarine, cerulean blue, mineral violet and lead sesquioxide, metal powder pigments such as zinc powder, iron powder and copper powder, sulfide pigments such as zinc sulfide, cadmium red, mercury sulfide, selenium red and cadmium yellow, chromate pigments such as molybdenum red, barium yellow, strontium yellow and chromium yellow, and ferrocyanide pigments such as Milori blue.

Preferable inorganic pigments are magnetic materials such as magnetite and ferrite. Organic pigments include the compounds listed in the Color Index. Cyan or green pigments include C.I. Pigment Blue 15, C.I. Pigment Blue 15:2, C.I. Pigment Blue 15:3, C.I. Pigment Blue 16, C.I. Pigment Blue 60 and C.I. Pigment Green 7.

Magenta or red pigments include C.I. Pigment Red 2, C.I. Pigment Red 3, C.I. Pigment Red 5, C.I. Pigment Red 7, C.I. Pigment Red 15, C.I. Pigment Red 16, C.I. Pigment Red 48:1, C.I. Pigment Red 53:1, C.I. Pigment Red 57:1, C.I. Pigment Red 122, C.I. Pigment Red 123, C.I. Pigment Red 139, C.I. Pigment Red 144, C.I. Pigment Red 149, C.I. Pigment Red 166, C.I. Pigment Red 178 and C.I. Pigment Red 222.

Yellow or orange pigments include C.I. Pigment Yellow 12, C.I. Pigment Yellow 13, C.I. Pigment Yellow 14, C.I. Pigment Yellow 15, C.I. Pigment Yellow 17, C.I. Pigment Yellow 93, C.I. Pigment Yellow 94, C.I. Pigment Yellow 138 and C.I. Pigment Yellow 180.

Commonly used organic pigments are copper-phthalocyanine known as C.I. Pigment Blue 15:3, a cyan pigment, dimethylquinacridone known as C.I. Pigment Red 122, a magenta pigment, and disazo yellow known as C.I. Pigment Yellow, a yellow pigment.

Offset prevention agent such as low molecular polyethylene, low molecular polypropylene, oxidized polyethylene, oxidized polypropylene, acid-modified polyethylene, acid-modified polypropylene, and polyolefin waxes (e.g., HYTEC, produced by Toho Chemical Industry Co., Ltd.) can also be used.

It is also possible to use positive charge control agents such as nigrosine series electron donor dyes, metal salts of naphthenic acid or higher fatty acids, alkoxylated amines, quaternary ammonium salts, alkylamides, metal complexes, pigments and fluorinated activators, and negative charge control agents such as electron recipient organic complexes, chlorinated paraffin, chlorinated polyester and copper phthalocyanine sulfonylamine.

Each of these substances may be incorporated in the polymer at about 0.1 to 25% by weight.

Non-spherical particle formation reaction

The non-spherical particle of the present invention is produced by coagulation a number of polymer particles of the present invention. A coloring agent may be added in dispersion and combined with polymer particles at the same time as coagulation of the polymer particles. Preferably, the coloring agent is added at the same time as synthesis of the polymer particles of the present invention and the resulting polymer particles combined with the coloring agent are used, whereby coloring agent dispersibility improves markedly.

The non-spherical particle of the present invention can be obtained by adding a metal salt, as a coagulant, to the polymer particle dispersion of the present invention at a concentration exceeding the critical coagulation concentration while stirring the dispersion, then adding an infinitely water-soluble organic solvent, and heating the mixture at a temperature exceeding the Tg of the polymer particles.

In the present invention, the average particle size and particle size distribution of the non-spherical particles are determined according to coagulant concentration, addition concentration of the infinitely water-soluble organic solvent, and the degree of dissociation of the monomer unit of the polymer particle, having an ionic dissociating group. For example, when the temperature at which the infinitely water-soluble organic solvent is added and the degree of dissociation of the monomer unit of the polymer particle, having an ionic dissociating group, are constant, particle size increases with the increase in coagulant concentration, and vice versa. Similarly, when the coagulant concentration and the degree of dissociation of the monomer unit of the polymer particle, having an ionic dissociating group, are constant, particle size increases with the increase in the concentration of infinitely water-soluble organic solvent added, and vice versa. Also, when the degree of dissociation of the monomer unit of the polymer particle, having an ionic dissociating group, is varied, particle size decreases with the increase in the degree of dissociation, and vice versa.

Accordingly, in the present invention, any desired particle size can be obtained by adjusting the above three factors. Interaction of the three factors allows the obtainment of particles of very narrow particle size distribution.

Infinitely water-soluble organic solvent

The infinitely water-soluble organic solvent for the present invention is selected from those which do not dissolve the polymer particle of the present invention, with preference given to those which swell the polymer particle of the present invention. Such solvents include alcohols such as methanol, ethanol, 1-propanol, 2-propanol, 2-methyl-2-propanol, 2-methoxyethanol, 2-ethoxyethanol and 2-butoxyethanol, acetonitrile and dioxane. Preferably, alcohols are selected, with greater preference given to 2-propanol.

The amount of organic solvent added is chosen as appropriate according to type of solvent used, desired particle size, coagulant concentration, the presence or absence of a monomer unit having an ionic dissociating group in the polymer particle, and the degree of dissociation. Usually, the organic solvent is added to the polymer particle dispersion at 5 to 300% by volume.

Method of production

In the present invention, a required amount of a metal salt or an aqueous solution thereof is added to a polymer particle dispersion while stirring. Then an infinitely water-soluble organic solvent is added, and the mixture is heated within the temperature range from $-5°$ C. to $+50°$ C. relative to the glass transition point (Tg) of the polymer particle. These are the basic processes. The heating temperature preferably falls within the range from $+15°$ C. to $+25°$ C. relative to Tg. Additives may be added in any order without limitation.

Some examples of the production process of the present invention are given below.

Production method 1

1) While stirring a polymer particle dispersion, a salt or an aqueous solution thereof is added.

2) To the resulting salt/polymer particle mixture, an infinitely water-soluble organic solvent is added.

3) The salt/polymer particle mixture containing the organic solvent is added to water as necessary.

4) The mixture is heated within the temperature range from $-5°$ C. to $+50°$ C. relative to the Tg of the polymer particles to thermally melt the polymer particles to yield non-spherical particles.

Production method 2

1) While stirring a polymer particle dispersion, an infinitely water-soluble organic solvent is added.

2) To the resulting dispersion of the polymer particles in a mixture of water and infinitely water-soluble organic solvent, a salt or an aqueous solution thereof is added.

3) The salt/polymer particle mixture containing the organic solvent is added to water as necessary.

4) The mixture is heated within the temperature range from $-5°$ C. to $+50°$ C. relative to the Tg of the polymer particles to thermally melt the polymer particles to yield non-spherical particles.

Production method 3

1) While stirring a polymer particle dispersion, an aqueous solution of a salt is added.

2) To the resulting salt/polymer particle mixture, an infinitely water-soluble organic solvent is added.

3) The salt/polymer particle mixture containing the organic solvent is added to water as necessary.

4) The mixture is heated within the temperature range from $-5°$ C. to $+50°$ C. relative to the Tg of the polymer particles to thermally melt the polymer particles to yield non-spherical particles.

Production method 4

1) While stirring a polymer particle dispersion, an infinitely water-soluble organic solvent is added.

2) To the resulting mixture of the polymer particles and infinitely water-soluble organic solvent, a salt or an aqueous solution thereof is added.

3) The salt/polymer particle mixture containing the organic solvent is added to water as necessary.

4) The mixture is heated within the temperature range from $-5°$ C. to $+50°$ C. relative to the Tg of the polymer particles to thermally melt the polymer particles to yield non-spherical particles.

Production method 5

1) A mixture of an aqueous salt solution and an infinitely water-soluble organic solvent is added to a polymer particle dispersion, or the reverse operation is performed, while stirring.

2) The resulting mixture is heated within the temperature range from −5° C. to +50° C. relative to the Tg of the polymer particles to thermally melt the polymer particles to yield non-spherical particles.

All above procedures are performed under stirring conditions. Some modifications are included in this category of operations.

In the present invention, heating temperature is chosen over the range from −5° C. to +50° C. relative to the Tg of the polymer particle. Choosing heating temperature and time as appropriate allows particle shape control.

For example, when heating temperature is constant, the resulting particle is more truly spherical as heating time increases. As heating temperature increases, truly spherical particles are obtained more rapidly.

Some coefficients for particle shape expression have been proposed, including the degree of non-sphericity defined as follows:

Degree of non-sphericity=(BET specific surface area of non-spherical particle)/(surface area of non-spherical particle as calculated from average particle size on the assumption that the particle is truly spherical)

The non-spherical particle of the present invention has a degree of non-sphericity of not less than 1.1, as defined above. When the non-spherical particle is used as an electrophotographic toner, in particular, the degree of non-sphericity is normally about 1.1 to 5.0, preferably 1.2 to 3.5. When the non-spherical particle is used as a carrier for immobilizing a bioactive substance, it is preferable that the particle surface area be greater, as long as mechanical strength is sufficient. For this reason, the degree of non-sphericity is not less than 2.0, preferably 2.5 to 5.0.

Electrophotographic toner

The non-spherical particles of the present invention can be used as an electrophotographic toner. When the non-spherical particle is used as an electrophotographic toner, its average particle size is preferably about 3 to 25 μm. The non-spherical particle of the present invention is particularly preferred for use as a toner of small particle size because it meets with no change in particle size distribution, remaining small in particle size, and because it can be obtained at high yield even without posttreatments such as classification. It is particularly preferable that the average particle size be about 5 μm. The non-spherical particle of the present invention contains a pigment and/or a dye as a coloring agent. The non-spherical particle of the present invention can also contain a charge control agent for controlling the amount of charges and an offset prevention agent, though these additives are not essential. For example, the non-spherical particle of the present invention may contain a monomer unit having an ionic dissociating group. Increasing the degree of dissociation of the monomer unit containing the ionic dissociating group results in an increased amount of charge of the non-spherical particle. It is also possible to set the amount of charge at any level by increasing the content of the monomer unit containing an ionic dissociating group.

The degree of non-sphericity as defined by the above-described coefficient is preferably about 1.1 to 5.0, more preferably about 1.2 to 3.5.

Although these non-spherical particles may be used as a toner singly, silica, titanium oxide, aluminum oxide and hydrophobic products thereof may be used as fluidizing agents in combination. It is preferable that the fluidizing agent be added at 0.01 to 20 parts by weight per 100 parts by weight of toner. There may also be added lubricants, including metal salts of higher fatty acids, such as cadmium salt, barium salt, nickel salt, cobalt salt, strontium salt, copper salt, magnesium salt and calcium salt of stearic acid, zinc salt, manganese salt, iron salt, cobalt salt, copper salt, lead salt and magnesium salt of oleic acid, zinc salt, cobalt salt, copper salt, magnesium salt, silicon salt and calcium salt of palmitic acid, zinc salt, cobalt salt and calcium salt of linolic acid, zinc salt and cadmium salt of ricinoleic acid, lead salt of caprylic acid and lead salt of caproic acid. These are added as necessary.

Carrier for immobilizing bioactive substance

The non-spherical particle of the present invention can be used as a carrier for immobilizing a bioactive substance. The bioactive substance for the present invention is exemplified by enzymes, antigens, antibodies, receptors, deoxyribonucleic acids and ribonucleic acids. For example, an enzyme is chemically or physically immobilized on the surface of the non-spherical particle of the present invention to yield an immobilized enzyme. Enzyme-immobilized non-spherical particles according to the present invention are packed in a column equipped with a warming jacket, the jacket is adjusted to a temperature optimized for the enzyme (e.g., 37° C.), the column is filled with a buffer of optimum pH and ionic strength, an enzyme substrate is added, and the enzyme reaction product is taken out from the column after completion of the reaction. The particle can be thus used as a reactor. Also, using a number of enzymes in combination, an immobilized enzyme for analytical purposes can be prepared. For example, for analyzing a sample for glucose, non-spherical particles according to the present invention, on which glucose oxidase (GOD) and peroxidase (POD) have been immobilized, are packed in a column, the column is filled with a 0.2M phosphate buffer of pH 7.0, the glucose-containing sample and a chromophobe (e.g., diaminobenzidine) are added, and the color change or concentration change in the chromophore is determined from a calibration curve previously prepared from a series of glucose solutions of known concentrations, to obtain the glucose concentration of the sample.

Enzyme immunoassay based on antigen-antibody reaction, receptor assay and complementary binding reactions of DNA or RNA can also be used.

The non-spherical particle of the present invention can also be used as a carrier for latex coagulation reactions, coagulation inhibiting reactions and other antigen-antibody reactions.

It is preferable that the average particle size of the non-spherical particles be 25 to 100 μm for use as a reactor, or 0.3 to 1.5 μm for use as a carrier for coagulation reactions. It is preferable that the degree of non-sphericity be as high as possible because the surface area increases as the degree of non-sphericity increases for the same particle size, as long as mechanical strength is sufficient. The degree of non-sphericity is not less than 2.0, preferably 2.5 to 5.0.

The present invention is hereinafter described in more detail by means of the following examples, which are not to be construed as limitative.

EXAMPLES

Example 1

Synthesis of polymer particles

To a 500 ml four-necked flask equipped with a cooling tube, a thermometer, a stirrer and a nitrogen blower, 300 ml of degassed deionized water and 1.8 g of Triton-770 (sodium alkylphenoxypolyethoxysulfonate, obtained from Rohm & Hass) were added, and 36 g of styrene, 6.75 g of n-butyl acrylate and 2.25 g of methacrylic acid were added. While stirring the mixture at a stirring rate of 250 rpm, nitrogen was blown in. After the internal temperature was raised to 70° C., an aqueous initiator solution, prepared by dissolving 1.8 g of potassium persulfate in 50 ml of degassed deionized water, was added, and a polymerization reaction was carried out in a nitrogen gas stream at 70° C. for 7 hours, after which the reaction mixture was filtered through a No. 3 glass filter to yield polymer particles. The polymer particles were applied to a light scattering electrophoretic particle size analyzer ELS-800 (produced by Otsuka Electronics Co.) to determine the particle size. The average particle size was 0.06 μm.

Polymerization was carried out in the same manner as above, except that the monomer composition was changed to 40.5 g of styrene and 4.5 g of acrylic acid. Particle size was determined in the same manner as above using ELS-800, the average particle size being 0.04 μm.

Polymerization was carried out in the same manner as above, except that the monomer composition was changed to 45 g of styrene alone. Particle size was determined in the same manner as above using ELS-800, the average particle size being 0.12 μm.

These samples, designated as P-01, P-02 and P-03, respectively, analyzed using potassium chloride by a conventional method, were found to have critical coagulation concentrations of 0.25 mol/l, 0.28 mol/l and 0.24 mol/l, respectively.

Synthesis of polymer particles combined with coloring agent

To an aqueous solution of 0.346 g of sodium dodecyl sulfate in 50 ml of deionized water, 1.62 g of carbon black (Regal 330R, produced by Cabot Corporation) was added to yield a dispersion. The average particle size of the carbon black in the dispersion was 0.08 μm.

This dispersion was added to a 500 ml four-necked flask equipped with a cooling tube, a thermometer, a stirrer and a nitrogen blower, and 150 ml of degassed deionized water and 20.25 g of a monomer (monomer composition shown in Table 1) were added. While stirring the mixture at a stirring rate of 500 rpm in a nitrogen gas stream, the internal temperature was raised to 70° C. After an aqueous solution of 1.125 g of potassium persulfate as a polymerization initiator in 50 ml of degassed deionized water was added at 70° C., polymerization was performed for 7 hours, after which the internal temperature was reduced to room temperature, and the reaction product was filtered through a No. 3 glass filter.

Polymerization was performed by the same reaction as above, except that different monomers, pigments, etc. were used. The results, along with those of the above-described synthesis of polymers, are given in Table 1 below.

TABLE 1

| | Monomer composition | Pigment (wt %) | Average particle size | Mw | Mw/Mn |
|---|---|---|---|---|---|
| P-1 | St/BA/MAA = 80/15/5 | — | 0.06 μm | $7.4 \times 10^4$ | 3.16 |
| P-2 | St/AA = 90/10 | — | 0.12 μm | $10.5 \times 10^4$ | 4.18 |
| P-3 | St/BA/MAA = 80/15/5 | CB (8 wt %) | 0.16 μm | $6.9 \times 10^4$ | 2.98 |
| P-4 | St/BA/MAA = 80/15/5 | PB-15:3 (8 wt %) | 0.21 μm | $7.2 \times 10^4$ | 3.18 |
| P-5 | St/BA/MAA = 80/15/5 | PR-122 (8 wt %) | 0.22 μm | $7.0 \times 10^4$ | 3.06 |
| P-6 | St/BA/MAA = 80/15/5 | PY-17 (8 wt %) | 0.24 μm | $7.1 \times 10^4$ | 3.28 |
| P-7 | St/BA/DMAEA = 80/15/5 | CB (8 wt %) | 0.18 μm | $6.8 \times 10^4$ | 3.42 |
| P-8 | St/BA/CMSt = 65/20/15 | CB (8 wt %) | 0.17 μm | $7.6 \times 10^4$ | 4.02 |

St:styrene, BA:n-butyl acrylate, MAA:methacrylic acid, AA:acrylic acid, DMAEA:N,N-dimethylaminoethyl acrylate, CMSt:chloromethylstyrene (vinylbenzyl chloride), CB:carbon black, PB-15:3:Pigment Blue 15:3, PR-122:Pigment Red 122, PY-17:Pigment Yellow 17.

Synthesis 1 of non-spherical particles

Using a 1N aqueous solution of sodium hydroxide, colored particles P-3 above were adjusted to obtain a sodium salt having a constant MAA content in the polymer particles, as determined using an conductivity measuring apparatus. The degree of dissociation was set at 5, 20, 50, 75 and 100%. Critical coagulation concentrations were determined using potassium chloride. A 100 ml portion of the thus-prepared polymer particle dispersion was added to a four-necked flask equipped with a stirrer, a cooling tube and a thermometer, and an aqueous solution of 2.98 g of potassium chloride in 50 ml of water was added while stirring at 250 rpm and room temperature, after which 50 ml of isopropanol and then 250 ml of water were added. After the internal temperature was raised to 85° C., the mixture was stirred at constant temperature for 6 hours. The potassium chloride concentration was 0.1 mol/l relative to the water added, or about 0.089 mol/l relative to the actual volume with isopropanol.

After completion of heating, the dispersion was analyzed for volume-average particle size ($d_{50}$), standard deviation ($\sigma_{50}$) and particle size distribution ($CV = \sigma_{50}/d_{50}$), using a particle size analyzer SALD-1100 (produced by Shimadzu Corporation). The results are given in Table 2.

TABLE 2

| | Degree of dissociation (%) | Critical coagulation concentration | $d_{50}$ | $\sigma_{50}$ | CV |
|---|---|---|---|---|---|
| PR-1 | 0 | 0.004 mol/l | 38.79 μm | 11.32 μm | 0.29 |
| PR-2 | 5 | 0.01 mol/l | 28.35 μm | 10.33 μm | 0.36 |
| PR-3 | 20 | 0.03 mol/l | 12.14 μm | 5.12 μm | 0.42 |
| PR-4 | 50 | 0.05 mol/l | 8.62 μm | 3.76 μm | 0.44 |
| PR-5 | 75 | 0.07 mol/l | 5.79 μm | 2.54 μm | 0.44 |
| PR-6 | 100 | 0.08 mol/l | 0.67 μm | 0.24 μm | 0.36 |

As shown in Table 2, by controlling the degree of dissociation of the monomer unit of the polymer particle, having a dissociating group, and adding a salt at a concentration exceeding the critical coagulation concentration of the polymer particle dispersion, it is possible to control average particle size and easily synthesize monodispersed non-spherical particles of narrow particle size distribution. Also, volume-based average particle size ($d_{50}$) and particle size distribution (CV) can be controlled mainly by the amount of salt added and the concentration of organic solvent used, respectively.

Synthesis 2 of non-spherical particles

Using a 1N aqueous solution of hydrochloric acid, colored particles P-7 above were adjusted to obtain a hydrochloride having a constant DMAEA content in the polymer particles as determined using an conductivity measuring apparatus. The degree of dissociation was set at 50%. Critical coagulation concentrations, determined using potassium chloride, zinc sulfate and aluminum chloride, were 0.2 mol/l for potassium chloride, $4.3 \times 10^{-3}$ mol/l for zinc sulfate and $3.4 \times 10^{-4}$ mol/l for aluminum chloride. A 100 ml portion of the thus-prepared polymer particle dispersion was added to a four-necked flask equipped with a stirrer, a cooling tube and a thermometer, and each metal salt was added to a concentration about double the critical coagulation concentration while stirring at 250 rpm and room temperature. Then 50 ml of n-propanol and then 300 ml of water were added. After the internal temperature was raised to 85° C., the mixture was heated at constant temperature for 6 hours while stirring.

After completion of heating, the dispersion was analyzed for volume-based average particle size ($d_{50}$), standard deviation ($\sigma_{50}$) and particle size distribution ($CV = \sigma_{50}/d_{50}$), using a particle size analyzer SALD-1100 (produced by Shimadzu Corporation). The results are given in Table 3. Data on the degree of non-sphericality are also given in Table 3.

TABLE 3

|      | $d_{50}$ | $\sigma_{50}$ | CV | Degree of non-sphericality |
|------|----------|---------------|------|--------------------------|
| PR-7 | 5.46 μm  | 2.57 μm       | 0.47 | 1.53                     |
| PR-8 | 5.66 μm  | 2.42 μm       | 0.42 | 1.49                     |
| PR-9 | 5.58 μm  | 2.49 μm       | 0.45 | 1.58                     |

From Table 3, it is seen that non-spherical particles of nearly constant average particle size distribution can be obtained by determining the amount of addition on the basis of the critical coagulation concentration of the polymer particle dispersion, even when metal salts of different valencies are used.

Synthesis 3 of non-spherical particles

Using a 1N aqueous solution of sodium hydroxide, each of polymer particle dispersions P-3 through P-7 was adjusted to obtain a sodium salt having a constant MAA content in the polymer particles as determined using an conductivity measuring apparatus. The degree of dissociation was set at 75%. The critical coagulation concentrations, determined using potassium chloride, were 0.07 mol/l for P-3 and 0.09 mol/l for P-4 through P-6. A 100 ml portion of each polymer particle dispersion was added to a four-necked flask equipped with a stirrer, a cooling tube and a thermometer, and an aqueous metal salt solution prepared by dissolving 6.04 g of potassium chloride in 50 ml of water was added while stirring at 250 rpm and room temperature. After which 50 ml of isopropanol and then 250 ml of water were added, the mixture was heated at 85° C. for 3 or 6 hours. After completion of heating, the dispersion was analyzed for average particle size ($d_{50}$), particle size distribution (CV) and the degree of non-sphericality. The results are given in Table 4 below.

TABLE 4

|       | 3-hr heating | | | 6-hr heating | | |
|-------|--------|------|---------------------|--------|------|---------------------|
|       | $d_{50}$ | CV | Degree of non-sphericality | $d_{50}$ | CV | Degree of non-sphericality |
| PR-10 | 5.12 μm | 0.43 | 2.35 | 6.24 μm | 0.41 | 1.23 |
| PR-11 | 4.18 μm | 0.42 | 3.15 | 5.68 μm | 0.45 | 1.51 |
| PR-12 | 4.89 μm | 0.48 | 3.44 | 5.89 μm | 0.51 | 1.42 |
| PR-13 | 4.99 μm | 0.44 | 2.83 | 5.75 μm | 0.48 | 1.78 |

From these results, it is seen that non only particle size but also the degree of non-sphericality can be controlled.

Synthesis of comparative non-spherical particles

By the method of Example 1 in Japanese Patent O.P.I. Publication No. 220358/1985 and the method of Example 2 in Japanese Patent O.P.I. Publication No. 284461/1992, comparative particles 1 and 2 were synthesized, both being non-spherical particles containing carbon black.

Using the same conditions as for PR-4, except that the organic solvent added was replaced with n-butanol or n-octanol, a reaction was carried out as directed under "Synthesis 1 of non-spherical particles", to yield comparative particles 3 and 4, respectively.

The results are given in Table 5 below.

TABLE 5

|                        | $d_{50}$ | CV | Degree of non-sphericality |
|------------------------|----------|------|--------------------------|
| Comparative particles 1 | 5.87 μm  | 1.98 | 5.86 |
| Comparative particles 2 | 5.37 μm  | 0.89 | 3.86 |
| Comparative particles 3 | 48.7 μm  | 2.49 | —    |
| Comparative particles 4 | 0.16 μm  | —    | —    |

It is evident that with respect to comparative particles 1 and 2, the particle size distribution is broad and the degree of non-sphericality is difficult to control. In the case of comparative particles 3, prepared using n-butanol, a partially water-soluble solvent, average particle size ($d_{50}$) could not be controlled, showing a very high value, and the particle size distribution was broad and uncontrollable. In the case of comparative particles 4, prepared using n-octanol, a hardly water-soluble solvent, the particle size obtained was exactly the same as the average particle size of PR-4 used, demonstrating the absence of particle growth.

These findings demonstrate that the comparative non-spherical particles have a broad particle size distribution and are difficult to control as to the degree of non-sphericality.

Example 2

To 100 parts by weight of each of inventive non-spherical particles PR-10 through PR-13 (used after a 3-hr or 6-hr reaction, with designation of PR-14 through PR-17 for 3-hr reacted particles) and comparative non-spherical particles 1 and 2, 2 parts by weight of hydrophobic silica and 1 part by weight of titanium oxide were added. Five parts by weight of the thus-obtained externally treated toner was mixed with 95 parts by weight of ferrite particles (carrier, average particle size 60 μm) whose surface was coated with a methyl methacrylate/styrene copolymer (MMA/St=7/3 by weight) to yield inventive developing agents 1 through 8 and comparative developing agents 1 and 2. Then, styrene/n-butyl acrylate (weight ratio=85/15) and 8 parts by weight of I carbon black were added, followed by kneading and milling, to yield a 5 μm toner, which was then treated in the same manner as above to yield comparative developing agent 3.

Using an electrophotographic copying machine U-Bix 3028, equipped with a heat roller fixer and a cleaning blade, each of the above developing agents was tested for resolution, fogging, offset resistance (hot offset temperature), toner coloring (degree of coloration), cleaning property and particle size distribution change. The results are given in Table 6 below.

Evaluations were made as follows:

1) Resolution

Copied images of a thin-line chart were taken, and the recognizable thin lines per mm were counted.

2) Fogging

A series of copied images were subjected to densitometry to determine the reflective densities for various colors on non-image portions using a Sakura Densitometer PDA-60, produced by Konica Corporation. A reflective density exceeding 0.02 was taken as indicating the onset of fogging, and fogging was evaluated by the number of copies taken before that time point.

3) Offset resistance (hot offset temperature, H temperature, in °C.)

Copied images were formed while step by step altering the fixing heat roller temperature setting, and the fixing roller temperature setting was obtained upon onset of toner stain due to the hot offset phenomenon, which temperature was taken as the offset temperature.

4) Toner coloration (toner reflective density)

The toner was attached to a white label in a single layer, and this toner layer was subjected to densitometry using a Sakura Densitometer PDA-60, to determine the reflective densities for various colors.

5) Cleaning property (CL property)

The surface of the photoreceptor was macroscopically observed, and the cleaning property was evaluated by the number of copies taken before onset of cleaning failure.

6) Changes over time in particle size distribution (% by volume)

The ratio by number (number %) of toner particles whose particle size was not larger than one-thirds of the volume-average particle size of all toner particles was determined initially (at actual imaging test initiation) and upon onset of fogging or after 50000 copies were taken (late stage). When the ratio by number increases above 10%, toner chargeability tends to be affected. Toner particle size was determined using a laser diffraction particle size analyzer SALD-1100, produced by Shimadzu Corporation.

yield non-spherical particles. These particles had an average particle size of $d_{50}=52$ μm, a standard deviation of $\sigma_{50}=11.4$ μm and a particle size distribution of $\sigma_{50}/d_{50}=0.22$.

With the same monomer composition as of P-2, 50 μm droplets were formed using calcium phosphate and sodium dodecyl benzenesulfonate as dispersing agents, after which the temperature was raised and suspension polymerization was performed to yield polymer particles (non-spherical particles). These particles had an average particle size of $d_{50}=51$ μm, a standard deviation of $\sigma_{50}=29.8$ μm and a particle size distribution of $\sigma_{50}/d_{50}=0.58$.

After filtration, washing and drying, these particles were re-dispersed in 0.5 mol/l phosphate buffer (pH 7.2), and DCC and glucoamylase were added, followed by a 24-hr reaction at 5° C. The reaction mixture was then filtered and washed with 0.5 mol/l phosphate buffer (pH 7.2). These glucoamylase-immobilized particles were filled in a column equipped with a constant temperature jacket, and an aqueous solution of oligosaccharide (0.5 mol/l phosphate buffer, pH 7.5) was passed through the column while keeping a temperature of 37° C. Five hours later an aliquot of the aqueous solution of oligosaccharide was assayed for glucose content by high performance liquid chromatography. The glucose conversion rate was 98% when the carrier of the present invention was used, while the conversion rate from the

TABLE 6

|  | Inv. 1 | Inv. 2 | Inv. 3 | Inv. 4 | Inv. 5 | Inv. 6 | Inv. 7 | Inv. 8 | Comp. 1 | Comp. 2 | Comp. 3 |
| --- | --- | --- | --- | --- | --- | --- | --- | --- | --- | --- | --- |
| Resolution | 19 | 20 | 18 | 17 | 20 | 19 | 19 | 18 | 15 | 14 | 17 |
| Fogging | 90000 | 90000 | 100000 | 90000 | 80000 | 100000 | 100000 | 90000 | 50000 | 40000 | 50000 |
| H temperature | 230 | 220 | 225 | 230 | 230 | 220 | 225 | 230 | 230 | 230 | 235 |
| Degree of coloring | 1.32 | 1.29 | 1.30 | 1.26 | 1.31 | 1.29 | 1.30 | 1.28 | 1.10 | 1.05 | 1.23 |
| CL property | 90000 | 100000 | 100000 | 90000 | 80000 | 90000 | 80000 | 70000 | 40000 | 40000 | 50000 |
| Initial ratio by number | 1.9 | 1.4 | 2.0 | 2.3 | 1.4 | 1.6 | 1.8 | 1.8 | 13.5 | 9.8 | 11.5 |
| Final ratio by number | 2.3 | 1.8 | 2.4 | 2.8 | 1.5 | 1.7 | 2.0 | 1.9 | 20.3 | 15.7 | 18.3 |

Inv.: Inventive   Comp.: Comparative

*FIGS. for fogging in inventive developing agents are expressed by the number of copies taken before discontinuation of the testing despite the absence of fogging.
*FIGS. for cleaning property in inventive developing agents are expressed by the number of copies taken before discontinuation of the testing despite the absence of cleaning failure.

From the results given in Table 6, it is seen that developing agents 1 through 8, all prepared from the toner of the present invention, possess excellent properties.

Inventive developing agents 1 through 8, in particular, have a sharp toner particle size distribution with little changes over time in particle size distribution, by far surpassing comparative developing agents 1 through 3 in durability.

Example 3

To an autoclave, 100 ml of a dispersion of polymer particles P-2 as 10% dissociated in 1N sodium hydroxide (degree of dissociation confirmed using a conductivity measuring apparatus) was added, and while stirring the dispersion at 250 rpm and room temperature, 10 ml of n-butyl alcohol and 25 ml of isopropyl alcohol were added drop by drop in that order, followed by a 3-hr reaction at 120° C., to comparative carrier was 43%, demonstrating that the carrier of the present invention is excellent.

The present invention provides non-spherical particles suitable for use as a toner for developing electrostatic images for electrophotography, electrostatic recording, electrostatic printing and other fields, or a carrier for immobilizing a bioactive substance.

What is claimed is:

1. A method for the production of non-spherical particles for an electrophotographic toner, each of the non-spherical particles comprising a plurality of polymer particles, wherein said non-spherical particles have a volume average particle size of 3 through 25 μm, said method comprising addition of a coagulant or an aqueous solution thereof, and an organic solvent which is infinitely miscible with water, to a polymer particle dispersion, a concentration of said coagulant being at least a critical coagulation concentration of said dispersion, thereafter, heating said dispersion containing said coagulant and said organic solvent to a predetermined temperature to coagulate said polymer particles.

2. The method of claim 1 wherein said coagulant is a metal salt.

3. The method of claim 2 wherein said metal salt is selected from the group consisting of alkali metal salts, alkaline earth metal salts, trivalent metal salts, manganese salts, and copper salts.

4. The method of claim 3 wherein said metal salt is selected from the group consisting of sodium chloride, potassium chloride, lithium chloride, calcium chloride, zinc chloride, copper sulfate, magnesium sulfate, manganese sulfate, aluminum chloride, and iron chloride.

5. The method of claim 1, wherein said polymer particles are combined with at least one compound selected from the group consisting of a pigment, a dye, an offset prevention agent and a charge control agent.

6. The method of claim 1, wherein said polymer particles are not dissolved in said organic solvent.

7. The method of claim 1 wherein said organic solvent is selected from the group consisting of alcohols, nitriles, and dioxane.

8. The method of claim 7 wherein said organic solvent is selected from the group consisting of methanol, ethanol, propanol, isopropanol, t-butanol, methoxyethanol, ethoxyethanol, butoxyethanol, acetonitrile, and dioxane.

9. The method of claim 8 wherein said organic solvent is 2-propanol.

10. The method of claim 1 wherein said organic solvent is introduced in an amount of 1% to 300% of said dispersion.

11. The method of claim 1 wherein said non-spherical particles have a degree of non-sphericality of 1.1 to 5.0.

12. The method of claim 1 wherein said predetermined temperature is from Tg–5° C. to Tg +50° C., wherein said Tg is a glass transition temperature of said polymer particles.

13. The method of claim 12 wherein said predetermined temperature is from Tg +15° C. and Tg +25° C.

14. The method of claim 1 wherein said metal salt is selected from the group consisting of alkali metal salts, alkaline earth metal salts, trivalent metal salts, manganese salts, and copper salts;

said organic solvent is selected from the group consisting of methanol, ethanol, propanol, isopropanol, t-butanol, methoxyethanol, ethoxyethanol, butoxyethanol, acetonitrile, and dioxane;

said organic solvent is introduced in amount of 1% to 300% of said dispersion; and said non-spherical particles have a degree of non-sphericality of 1.1 to 5.0.

15. The method of claim 1 wherein said non-spherical particles are a carrier for immobilizing a bioactive substance.

16. The method of claim 15 wherein said bioactive substance is selected from the group consisting of enzymes, antigens, antibodies, receptors, deoxyribonucleic acid, ribonucleic acid, and mixtures thereof.

17. The method of claim 1 wherein said polymer particles are from a monomer having an ionic dissociating group.

18. The method of claim 17 wherein at least part of said ionic groups is dissociated.

* * * * *